United States Patent
Le Ruyet et al.

(10) Patent No.: US 11,473,050 B2
(45) Date of Patent: Oct. 18, 2022

(54) METHOD FOR THE PROTEIN ENRICHMENT OF MICROALGAL BIOMASS

(71) Applicant: Corbion Biotech, Inc., South San Francisco, CA (US)

(72) Inventors: Marie Le Ruyet, Lille (FR); Laurent Segueilha, Marquette lez Lille (FR); Mélanie Cappe, Merville (FR); Sylvain Delaroche, Longuenesse (FR)

(73) Assignee: Corbion Biotech, Inc., South San Fransisco, CA (US)

( * ) Notice: Subject to any disclaimer, the term of this patent is extended or adjusted under 35 U.S.C. 154(b) by 825 days.

(21) Appl. No.: 16/074,251

(22) PCT Filed: Feb. 8, 2016

(86) PCT No.: PCT/FR2016/050269
§ 371 (c)(1),
(2) Date: Jul. 31, 2018

(87) PCT Pub. No.: WO2017/137668
PCT Pub. Date: Aug. 17, 2017

(65) Prior Publication Data
US 2019/0345435 A1    Nov. 14, 2019

(51) Int. Cl.
| C12N 1/12 | (2006.01) |
|---|---|
| A23L 17/60 | (2016.01) |
| A23L 33/195 | (2016.01) |
| A23J 1/00 | (2006.01) |
| A23J 3/20 | (2006.01) |
| C12N 1/38 | (2006.01) |
| C12P 13/10 | (2006.01) |
| C12P 13/14 | (2006.01) |
| C12P 21/00 | (2006.01) |

(52) U.S. Cl.
CPC .............. *C12N 1/12* (2013.01); *A23J 1/009* (2013.01); *A23J 3/20* (2013.01); *A23L 17/60* (2016.08); *A23L 33/195* (2016.08); *C12N 1/38* (2013.01); *C12P 13/10* (2013.01); *C12P 13/14* (2013.01); *C12P 21/00* (2013.01)

(58) Field of Classification Search
CPC ........... C12P 21/00; C12P 13/10; C12P 13/14; C12N 1/38; C12N 1/12; C12N 1/125; A23J 3/20; A23J 1/009; A23L 33/195; A23L 17/60
See application file for complete search history.

(56) References Cited

U.S. PATENT DOCUMENTS

| 2,949,700 A | 8/1960 | Kathrein |
|---|---|---|
| 3,108,402 A | 10/1963 | Kathrein |
| 3,142,135 A | 7/1964 | Kathrein |
| 4,564,526 A | 1/1986 | Takashima |
| 5,547,699 A | 8/1996 | Iizuka et al. |
| 5,792,631 A | 8/1998 | Running |
| 5,912,113 A | 6/1999 | Nakamura et al. |
| 2007/0099280 A1 | 5/2007 | Barclay |
| 2007/0167396 A1 | 7/2007 | Dillon et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2012/0128851 A1 | 5/2012 | Brooks et al. |
| 2013/0122180 A1 | 5/2013 | Brooks et al. |
| 2016/0046900 A1* | 2/2016 | Macquart ................ C12N 1/12 435/71.1 |
| 2016/0143336 A1 | 5/2016 | Druon et al. |
| 2016/0161460 A1 | 6/2016 | Druon et al. |
| 2016/0192691 A1 | 7/2016 | Druon et al. |
| 2016/0208212 A1 | 7/2016 | Delaroche et al. |
| 2016/0324167 A1 | 11/2016 | Brooks et al. |
| 2016/0326483 A1 | 11/2016 | Segueilha et al. |

(Continued)

FOREIGN PATENT DOCUMENTS

| CN | 101230364 A | 7/2008 |
|---|---|---|
| CN | 102618431 | 8/2012 |

(Continued)

OTHER PUBLICATIONS

Hellebust et al., Biol. Ocean., 6(3-4):241-255 (1989) (Year: 1989).*
Cho et al., Planta, 162:23-29 (1984) (Year: 1984).*
Wu et al., Curr. Op. Clin. Nutr. Metabol. Care, 3:59-66 (2000) (Year: 2000).*
Agirman et al., FEB, 24(11):3643-3648 (2015) (Year: 2015).*
Hiller, J. Exp. Bot., 15(43):15-20 (1964) (Year: 1964).*
McAuley, New Phytol., 104:415-427 (1986) (Year: 1986).*
McAuley, Planta, 171:532-538 (1987) (Year: 1987).*
Schlee et al., Planta, 168:232-238 (1986) (Year: 1986).*
Pelley et al., J Phycol., 15:110-112 (1979) (Year: 1979).*

(Continued)

*Primary Examiner* — Renee Claytor
*Assistant Examiner* — Tiffany M Gough
(74) *Attorney, Agent, or Firm* — Leydig, Voit & Mayer (57) ABSTRACT

The invention relates to a method for the protein enrichment of a heterotrophically cultured microalga, the microalga being of the genus *Chlorella*, even more particularly *Chlorella protothecoides*, characterized in that it comprises:
  a first step directed toward limiting the ammonium supply so as to obtain a microalgal biomass with a protein content of less than 50% expressed as N.6.25, preferably less than 30%, more preferentially between 20 and 25%;
  a second step in which the ammonium supply in the fermentation medium is increased so as to obtain a protein content of greater than 50%, preferably greater than 60%, more preferentially greater than 65%.

19 Claims, 5 Drawing Sheets

(56) References Cited

U.S. PATENT DOCUMENTS

| | | | |
|---|---|---|---|
| 2016/0340640 | A1 | 11/2016 | Macquart et al. |
| 2016/0376544 | A1 | 12/2016 | Cossart et al. |
| 2018/0000116 | A1* | 1/2018 | Guillemant .......... C07K 14/405 |
| 2018/0139994 | A1 | 5/2018 | Brooks et al. |

FOREIGN PATENT DOCUMENTS

| | | |
|---|---|---|
| EP | 1 359 224 A1 | 11/2003 |
| EP | 1 724 357 | 11/2006 |
| EP | 2 248 906 | 11/2010 |
| FR | 1356113 | 3/1964 |
| FR | 2 924 126 A1 | 5/2009 |
| FR | 3 008 873 A1 | 10/2014 |
| JP | 360075244 | 10/1983 |
| JP | 409252707 A | 9/1997 |
| WO | WO 91/18108 | 11/1991 |
| WO | WO 2010/045368 | 4/2010 |
| WO | WO 2010/120923 | 10/2010 |
| WO | WO 2011/130578 A2 | 10/2011 |
| WO | WO 2012/063137 | 5/2012 |
| WO | WO 2014/074769 A2 | 5/2014 |
| WO | WO 2014/117163 A1 | 7/2014 |
| WO | WO 2014/154787 | 10/2014 |
| WO | WO 2014/207376 | 12/2014 |
| WO | WO 2014/207377 | 12/2014 |
| WO | WO 2015/011428 | 1/2015 |
| WO | WO 2015/022469 | 2/2015 |
| WO | WO 2015/025111 | 2/2015 |
| WO | WO 2015/079182 | 6/2015 |
| WO | WO 2015/107312 | 7/2015 |
| WO | WO 2017/137668 | 8/2017 |

OTHER PUBLICATIONS

Chacón-Lee et al., "Microalgae for "Healthy" Foods—Possibilities and Challenges," Comp. Rev. Food Sci. and Safety, 9: 655-675 (2010).
"Enter the World of Microalgae," Roquette (Jun. 2014).
International Bureau, International Preliminary Report on Patentability in International Application No. PCT/FR2016/050269, dated May 9, 2016.
International Bureau, International Search Report in International Application No. PCT/FR2016/050269, dated May 9, 2016.
Non-Final Rejection, dated Jan. 11, 2017, in U.S. Appl. No. 14/779,365.
Final Rejection, dated Sep. 14, 2017, in U.S. Appl. No. 14/779,365.
Non-Final Rejection, dated Apr. 27, 2018, in U.S. Appl. No. 14/779,365.
Non-Final Rejection, dated Jul. 28, 2017, in U.S. Appl. No. 14/911,078.
Final Rejection, dated Jan. 26, 2018, in U.S. Appl. No. 14/911,078.
Restriction Requirement, dated Oct. 30, 2017, in U.S. Appl. No. 14/911,743.
Non-Final Rejection, dated Jun. 6, 2018, in U.S. Appl. No. 14/911,743.
Non-Final Rejection, dated Apr. 13, 2017, in U.S. Appl. No. 14/913,383.
Final Rejection, dated Dec. 26, 2017, in U.S. Appl. No. 14/913,383.
Non-Final Rejection, dated Jan. 13, 2017, in U.S. Appl. No. 15/039,428.
Final Rejection, dated Jul. 11, 2017, in U.S. Appl. No. 15/039,428.
Non-Final Rejection, dated Jan. 5, 2018, in U.S. Appl. No. 15/039,428.
Restriction Requirement, dated Jan. 19, 2017, in U.S. Appl. No. 15/112,436.
Non-Final Rejection, dated Apr. 6, 2017, in U.S. Appl. No. 15/112,436.
Final Rejection, dated Oct. 16, 2017, in U.S. Appl. No. 15/112,436.
International Search Report, dated Sep. 30, 2014, from International Patent Application No. PCT/EP2014/056125, pp. 1-8.
Written Opinion of the Searching Authority, dated Sep. 30, 2014, from International Patent Application No. PCT/EP2014/056125, pp. 1-8.
International Search Report, dated Nov. 24, 2014, from International Patent Application No. PCT/FR2014/051943.
Written Opinion of the Searching Authority, dated Nov. 24, 2014, from International Patent Application No. PCT/FR2014/051943.
International Search Report, dated Feb. 11, 2015, from International Patent Application No. PCT/FR2014/052081.
Written Opinion of the Searching Authority, dated Feb. 11, 2015, from International Patent Application No. PCT/FR2014/052081.
International Search Report, dated Nov. 20, 2014, from International Patent Application No. PCT/FR2014/052113.
Written Opinion of the Searching Authority, dated Nov. 20, 2014, from International Patent Application No. PCT/FR2014/052113.
International Search Report, dated Mar. 10, 2015, from International Patent Application No. PCT/FR2014/053075.
Written Opinion of the Searching Authority, dated Mar. 10, 2015, from International Patent Application No. PCT/FR2014/053075.
International Search Report, dated Jun. 1, 2015, for International Patent Application No. PCT/FR2015/050123, pp. 1-14.
Written Opinion, dated Jun. 1, 2015, for International Patent Application No. PCT/FR2015/050123, pp. 1-14.
International Search Report, dated Sep. 5, 2016, from International Patent Application No. PCT/FR2016/050269, filed Feb. 8, 2016, and English Translation.
Written Opinion of the Searching Authority, dated Sep. 5, 2016, from International Patent Application No. PCT/FR2016/050269, filed Feb. 8, 2016. No Translation.
French Application No. FR 1550570, French Search Report and Written Opnion, dated Oct. 21, 2015.
Chinese Patent Application No. 201480039481.5, Notification of First Office Action, dated Jul. 5, 2017.
Chinese Patent Application No. 201480039481.5, Notification of Second Office Action, dated May 9, 2018.
Japanese Patent Application No. JP 2016-533941, English Translation of the Notice of Reasons for Rejection, dated May 21, 2018.
European Patent Application No. EP3036316, First Examination Report, dated Oct. 10, 2017. (in French).
Japanese Patent Application No. JP 2016-535517, English Translation of the Notice of Reasons for Rejection, dated May 21, 2018.
Albuquerque, M.G.E., et al., "Strategies for the development of a side stream process for polyhydroxyalkanoate (PHA) production form sugar case molasses." Journal of Biotechnology (2007), 130: 411-421, Specif. pp. 412, 415, 417.
Anderson, *Algal Culturing Techniques*, Elsevier, (2005), Part 1.
Anderson, *Algal Culturing Techniques*, Elsevier, (2005), Part 2, with Examiner's Notes, p. 433.
Becker, E.W., "Micro-algae as a source of protein," Biotechnology Advances,vol. 25; No. 2, pp. 207-201, (Jan. 26, 2007).
Belasco, Warren, "Algae Burgers for a Hungry World? The Rise and Fall of Chlorella Cuisine," Technology and Culture, 38(3):608-634, (1997).
Brown, M.R., et al. "Biochemical composition of microalgae from the green algal classes Chlorophyceae and Prasinophyæae. 1. Amino acids, sugars and pigments" *Journal of Experimental Marine Biology and Ecology*, (Oct. 12, 1992), 161(1), 91-113.
Chacón-Lee, T.L. and G.E. González-Mariño, "Microalgae for "Healthy" Foods—Possibilities and Challenges", Comprehensive Reviews in Food Science and Food Safety, vol. 9; (Oct. 31, 2010), pp. 655-675.
Chen et al., (1991) "Effect of C/N ratio and aeration on the fatty acid composition of heterotrophic *Chlorella sorokiniana,*" *Journal of Applied Phycology*, 3:203-209.
Chen, Y.H., et al., "Fed-batch fermentation and supercritical fluid extraction of heterotrophic microalgal *Chlorella protothecoides* lipids", Bioresource Technology, Jun. 1, 2012), vol. 114, pp. 512-517.
Doucha , J. et al., "Production of High-density Chlorella culture grown in fermenters", Journal of Applied Phycology, Jan. 12, 2011, vol. 24, No. 1, pp. 35-43.
Guccione, Alessia et al., "Chlorella for protein and biofuels: from strain selection to outdoor cultivation in a Green Wall Panel photobioreactor", Biotechnology for Biofuels, Biomed Central, Ltd, GB, (Jun. 7, 2014), vol. 8, No. 1, p. 84.

(56) References Cited

OTHER PUBLICATIONS

Harms, P., et al., "Bioprocessing monitoring", *Current Opinion in Biotechnology*, Apr. 1, 2002, vol. 13, No. 2, pp. 124-127.
Ji, Y. et al. "Differential effects of phosphorus limitation on cellular metals in Chlorella and Microcystis" Limnology and Oceanography, (Sep. 1, 2008), vol. 53, No. 5., pp. 1790-1804.
Kliphuis, A.M.J. et al., "Light respiration in Chlorella sorokiniana", Journal of Applied Phycology, (2011), 23:935-947 (specif. pp. 935, 937, 938, 945).
Krüger, "Kurze Charakteristik einiger niedrerer Organismen im Saftfluss der Laubbäume," Hedwigia, 33: 241-266, (1894). Machine Translation.
Li, Xiufeng, et al., "Large-scale biodiesel production from microalga *Chlorella protothecoides* through heterotrophic cultivation in bioreactors," Biotechnology and Bioengineering, 98(04):764-771, (Nov. 1, 2007).
Mattes, R.D., "Is there a fatty acid taste?" Annual Review of Nutrition, (2009), 29:305-327 (cited pre-pub manuscript, pp. 1-24, specif. p. 7).
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of *Chlorella protothecoides*," J. Biotech., 110:85-93, (2004).
Perez-Garcia, O. et al., "Heterotrophic cultures of microalgae: Metabolism and potential products", Water Research, Jan. 1, 2011, vol. 45, No. 1, pp. 11-36.
Pleissner, D. et a l. "Effects of Phosphorous, Nitrogen, and Carbon Limitation on Biomass Composition in Batch and Continuous Flow Cultures of the Heterotrophic Dinoflagellate Crypthecodinium cohnii", Biotechnology and Bioengineering, Aug. 2012,pp. 2005-2016, vol. 109, No. 8.
Qianran, Ma et al., "The Fermenter High Density Heterotrophic Culture of Chlorella", Guangdong Chemical Industry, (Feb. 28, 2013), Issue 40, vol. 4 (English Abstract Only).
Qu, C.-B. et al. "Phosphate assimilation by Chlorella and adjustment of phosphate concentration in basal medium for its cultivation" Biotechnology Letters, Oct. 20, 2008, pp. 1735-1740, vol. 30, No. 10.
Rhee, G-Yull, "Effects of N:P Atomic Ratios and Nitrate Limitation on Algal Growth, Cell Composition, and Nitrate Uptake", Limnology and Oceanography, vol. 23, No. 1 (Jan. 1978), pp. 10-25.
Samarasinghe, Nalin, et al., "Algal Cell Rupture Using High Pressure Homogenization as a Prelude to Oil Extraction." Renewable Energy, vol. 48, (Apr. 20, 2012) pp. 300-308, 2012.
Sansawa, H. et al., "Production of Intracellular Phytochemicals in Chlorella under Heterotrophic Conditions," Journal of Bioscience and Bioengineering, 98(6):437-444, (Jan. 1, 2004).
Shi et al., "Production and rapid extraction of lutein and the other lipid-soluble pigments from *Chlorella protothecoides* grown under heterotrophic and mixotrophic conditions," Nahrung, 43:109-113, (1999).
Shi, et al., "Production of biomass and lutein by *Chlorella protothecoides* at various glucose concentrations in heterotrophic cultures", Process Biochemistry, 34:341-347, (1999).
Shi, X. M. et al., "High-Yield Production of Lutein by the Green Microalga *Chlorella protothecoides* in Heterotrophic Fed-Batch Culture," Biotechnol. Prog., 18(4):723-727 (2002).
Shihira-Ishikawa, I., et al., "Nutritional Control of Cell Pigmentation In *Chlorella protothecoides* With Special Reference to The Degeneration of Chloroplast Induced by Glucose," Plant and Cell Physiology, 5(2):227-240 (Feb. 1, 1964), [online abstract], Retrieved on Jun. 3, 2010 from http://pcp.oxfordjounals.org/cgi/content/abstract/5/2/227.
Suh, I.S. et al., "Photobioreactor Engineering: Design and Performance", Biotechnology and Bioprocess Engineering, (Jan. 1, 2003), vol. 8, No. 6, pp. 313-321.
Syrett, P.J., "The Assimilation of Ammonia by Nitrogen-Starved Cells of *Chlorella vulgaris*. Part II. The Assimilation of Ammonia to Other Compounds." Annals of Botany, vol. 17, pp. 21-36, 1953.
Syrett, P.J., "The Assimilation of Ammonia by Nitrogen-Straved Celled of *Chlorella vulgaris*. Part I: The Correlation of Assimilation with Respiration", Annals of Botany, Academic Press, London, GB,(Jan. 1, 1953), vol. 17, No. 1, pp. 1-19.
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic *Chlorella protothecoides*," Acta Botanica Sinica, 35(11):849-858, (1992).
Wu et al., "New Discoveries in Study on Hydrocarbons From Thermal Degradation of Heterotrophically Yellowing Algae," Science In China, 37(3):326-35, (Mar. 1, 1994).
Xiong et al., "High-density fermentation of microalga *Chlorella protothecoides* in bioreactor for microbio-diesel production," Appl. Microbiol. Biotechnol., 78:29-36, (2008).
Xu, H., et al., "High Quality Biodiesel Production from a Microalgal *Chlorella protothecoides* by Heterotrophic Growth in Fermenters." Journal of Biotechnology, vol. 126, pp. 499-507, (2006).
Zeng, A.P. et al., "Use of respiratory quotient as a control parameter for optimum oxygen supply and scale-up of 2,3-butanediol production under microaerobic conditions." Biotechnology and Bioengineering, (1994), 44:1107-1114.
Memorandum Order, *Roquette Frères, S.A. v. Solazyme, Inc.*, C.A. No. 14-1442-SLR, District Court for the District of Delaware, Jan. 12, 2016.
Plaintiff and Counter-Defendant Roquette Frères, S.A.'s Reply Brief in Support of Its Motion for Stay Pending Appeal, *Roquette Frères, S.A. v. Solazyme, Inc.*, C.A. No. 14-1442-SLR, District Court for the District of Delaware, Jan. 8, 2016.
Defendant and Counterclaimant Solazyme, Inc.'s Brief in Opposition To Plaintiff and Counter-Defendant Roquette Freres, S.A.'s Motion To Stay Pending Appeal, *Roquette Frères, S.A. v. Solazyme, Inc.*, C.A. No. 14-1442-SLR, District Court for the District of Delaware, Jan. 6, 2016.
Declaration of Jonathan Wolfson in Support of Defendant and Counterclaimant Solazyme, Inc.'s Opposition To Plaintiff and Counterclaimant Roquette Freres, S.A.'s Motion To Stay Pending Appeal, *Roquette Frères, S.A. v. Solazyme, Inc.*, C.A. No. 14-1442-SLR, District Court for the District of Delaware, Jan. 6, 2016, Redacted Public Version.
Declaration of Jeffrey M. Goehring in Support of Plaintiff and Counter-Defendant Roquette Frères, S.A.'s Brief Motion for Stay Pending Appeal, *Roquette Frères, S.A. v. Solazyme, Inc.*, C.A. No. 14-1442-SLR, District Court for the District of Delaware, Dec. 28, 2015, Redacted Version • Exhibit 1, BASF and Solazyme Launch the First Commercial Microalgae-Derived Betaine Surfactant, Solazyme, Inc., Jul. 28, 2015 • Exhibit 2, Solazyme Bunge Renewable Oils Completes Key Redundant Power and Steam Supplies, Solazyme Bunge Renewable Oils, Jun. 30, 2015 • Exhibit 3, Solazyme Receives FDA GRAS No Questions Letter for High Oleic Algae Oil, Solazyme, Inc., Feb. 24, 2015 • Exhibit 4, Solazyme's (SZYM) CEO Jonathan Wolfson on Q1 2015 Results—Earnings Call Transcript, Solazyme, Inc., May 6, 2015 • Exhibit 5, Solazyme's (SZYM) CEO Jonathan Wolfson on Q2 2015 Results—Earnings Call Transcript, Solazyme, Inc., Jul. 30, 2015 • Exhibit 6, Solazyme's (SZYM) CEO Jonathan Wolfson on Q4 2014 Results—Earnings Call Transcript, Solazyme, Feb. 26, 2015 • Exhibit 7, Redacted In Its Entirety.
Motion To Stay Pending Appeal and Order Granting Motion To Stay Pending Appeal, *Roquette Frères, S.A. v. Solazyme, Inc.*, C.A. No. 14-1442-SLR, District Court for the District of Delaware, Dec. 28, 2015.
Memorandum of Law in Support of Motion By Roquette Frères, S.A. for a Stay Pending Appeal, *Roquette Frères, S.A. v. Solazyme, Inc.*, C.A. No. 14-1442-SLR, District Court for the District of Delaware, Dec. 28, 2015.
Email dated Nov. 3, 2015, from Gerald Suh of Solazyme, Inc., to Jeffrey M. Goehring of Young & Thompson International Patent & Trademark Law (counsel for Roquette Frères, S.A.).
Letter dated Oct. 6, 2015, from Jeffrey M. Goehring of Young & Thompson International Patent & Trademark Law (counsel for Roquette Frères, S.A.) to Gerald Suh of Solazyme, Inc., and R.

(56) References Cited

OTHER PUBLICATIONS

James Balls and William E. McShane of Novak Druce Connolly Bove + Quigg LLP (counsel for Solazyme Roquette Nutritionals, LLC), which included the following enclosures: • Exhibits 1, 9-12, and 14-15 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 141, Jun. 22, 2015, Redacted Version • Exhibits 2-8 To the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112-1, Jun. 22, 2015 • Exhibit 13 To the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112-2, Jun. 22, 2015 • Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 112, Jun. 22, 2015 • Roquette Frères, S.A.'s Opening Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 140, Jun. 22, 2015, Redacted Version.
Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.
Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).
Opinion dated Dec. 21, 2015 in *Roquette Frères, S.A., v. Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.
Youzhi Jiagong, (Jun. 8, 2007), "Oil Processing Technology (2nd edition)", Chemical Industry Press, Title page, Publication Page, Table of Contents, pp. 206-213, (in Chinese).
"Linoleic acid and α-linolenic acid are real essential fatty acids", (Mar. 1998), Title page, Publication Page, Table of Contents, Chapter 2: Essential Fatty Acids (pp. 12-13) and Chapter 15: Selection of the most suitable fatty acids (pp. 89-91), with English translation.
Bowman, Barbara A. and Robert M. Russell (eds.), "Present Knowledge in Nutrition" (1st Edition), (Oct. 2004), Title page, Publication Page, Table of Contents, p. 231 (in Chinese).
"Auxenochlorella", article from Wikipedia, Retrieved from the Internet on Mar. 23, 2016, "https://en.wikipedia.org/w/index.php?title=Auxenochlorella&oldid=711518993".
Clore, G.M. and E.M. Chance, A computer analysis of cyanide stimulated oxygen uptake in *Chlorella protothecoides*. (Jul. 1977) FEBS Lett. 79 (2):353-356.
"Algen—Nudein ais Altmark Spezialitat (Algae noodles: a speciality from Altmark region)" in German language, and other *Chlorella* Food products, (Oct. 9, 2007), 3 pages.
Imai, Ichiro, et al. "Advanced research on Shellfish poisonings: Current Status and overview", Table of Contents, Chapters 1 and Chapter 4, 11 pages.

"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].
Lee, Yuan-Kun, "Commercial Production of microalgae in the Asia-Pacific rim", Journal of Applied Phycology, 9:403-411, (Oct. 29, 1997).
Kay, Robert A., "Microalgae as Food and Supplement", Critical Reviews in Food Science and Nutrition, 30(6):555-573 (Feb. 1991).
Usuki, Riichiro and Luniko Kamata, "Experimental Trials on the Role of Lipids in Good Taste and Good Body of Foods", Research reports of Shokei Gakuin College 53, May 2006, p. 85-90 (in Japanese with English Abstract).
"Chlorella Photosynthesis—Dictionary", last modified Mar. 23, 2015, Retrevied from the Internet: <URL: (http://photosyn.jp/pwiki/index.php?%E3%82%AF%E3%83%AD%E3%83%AC%E3%83%A9) with English Machine Translation.
Hirashima, Ryuta, "Framework of evaluation on inventive step requirement and significance of 'technical problem'", Patent 2010, 63(5): 34-49 (in Japanese; no translation).
Ullmann, Jorg, "The Difference between *Chlorella* vulgaris and *Chlorella* pyrenoidosa", (2006) (http://www.algomed.de/index.php?op=algenfarm_geschichte).
"History of the algae farm: Chlorella Algae—Roquette Klötze GmbH", [Retrieved from the Internet Nov. 25, 2016: <URL: (http://www.algomed.de/index.php?op=algenfarm_geschichte)].
Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.
Oral Summary, dated Nov. 7, 2016, for Invalidation Hearing for Japanese Patent No. 5731982 (in Japanese).
Oral Summary by the Patentee, dated Nov. 29, 2016, for Invalidation Hearing for Japanese Patent No. 5731982 (in Japanese).
USDA National Nutrient Database (https://ndb.nal.usda.gov/ndb/).
Environmental Stresses in Non Mammalian Organisms, p. 29. with English translation.
Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid *Chlorella protothecoides* S106 Flour GRAS Notification and GRAS Exemption Claim (dated Apr. 18, 2013).
Solazyme Market and Products, (2005).
Letter from Susan Cho to Susan Carlson, dated Jul. 25, 2011 and "RFl's *Chlorella vulgaris* GRAS Self affirmation (dated Jul. 16, 2010)."
[Retrieved from the Internet Oct. 13, 2016: <URL: http://hfnet.nih.go.jp/contents/detail105.htm] (in Chinese).
"*Roquette Freres, S.A.* and *Solazyme, Inc.* Agree to Dissolve Microalgae Join Venture", (Jun. 24, 2013) Press Release, Lestrem, France.
Standard Tables of Food Composition in Japan 2015 (Seventh Revised Edition), Table of Fatty Acid Composition, Edited by The Council for Science and Technology, the Ministry of Education, Culture, Sports, Science and Technology, (available from http://www.mext.go.jp/a_menu/syokuhinseibun/1365295.htm) [Retrieved from the Internet Oct. 12, 2016: <URL: (http://www.algomed.de/index.php?op=algenfarm_geschichte)] http://www.geocities.jp/jr2bvb/syokuhin/sibousan/oil_s.htm].
"'Taste' of Lipids?" [Retrieved from the Internet Oct. 12, 2016: <URL: (https://sites.google.com/site/coffeetambe/coffeescience/physiology/taste/fat] with English Machine Translation.
Japanese Laid-Open Publication No. 2000-175680 (translator's note: an English language member of the same patent family: EP 1142985 (A1)).
Japanese Laid-Open Publication No. 2002-223787 (translator's note: no English language counterpart could be located).
http://mcc.nies.go.jp/strainList.do?strainId=2555&condition=Auxenochlorella+protothecoides.
http://mcc.nies.go.jp/strainList.do?strainId=2568&condition=Auxenochlorella+protothecoides.
*Roquette Freres S.A. v. Solazyme Inc.*, Delaware District Court, Case No. 1:14-cv-01442 District Judge Sue L. Robinson, presiding,

(56) References Cited

OTHER PUBLICATIONS

Solazyme, INC.'s Answer to Plaintiff Roquette Freres, S.A.'s Complaint, Petition to Confirm Arbitration Award and Counterclaims, filed Feb. 26, 2015, 29 pages.
Joint Venture and Operating agreement of Solazyme Roquette Nutritionals, LLC., copy dated Nov. 7, 2015.
*Solazyme, Inc.* vs. *Roquette Freres, S.A.*, Arbitration Award, dated Feb. 19, 2015.
Request for Invalidation, dated Jan. 7, 2015, for Chinese Patent Application No. 200980149978.1, 21 pages (in Chinese).
Supplemental Statement for Request for Invalidation, dated Dec. 2, 2015, for Chinese Patent Application No. 200980149978.1, 35 pages (in Chinese), including the list of submitted Counter Evidences on p. 1-2.
Notification of Acceptance of Request for Invalidation, dated Jan. 28, 2016, for Chinese Patent Application No. 200980149978.1, 4 pages (in Chinese).
Documents filed by the Petitioner—Part II, dated Apr. 29, 2015, for Chinese Patent Application No. 200980149978.1, 21 pages (in Chinese), including : • Jia, Xuan, et al., "Removal of Total nitrogen form wastewater discharge from a chemical pertilizer plant by *Chlorella protothecoides* USTB-01", Chinese Journal of Environmental Engineering, (Apr. 2010), 4(4):737-740 (in Chinese).
Documents filed by the Petitioner—Part III, dated May 5, 2015, for Chinese Patent Application No. 200980149978.1, 21 pages (in Chinese), including : , including : • Singelton Paul and Diana Sainsbury, "Dictionary of Microbiological and Molecular Biology, (3rd Ed. 2006)", pp. 155 (and Chinese translation thereof) • Singelton Paul and Diana Sainsbury, "Dictionary of Microbiological and Molecular Biology, (2nd Ed. 1987)", pp. 178-179 (and Chinese translation thereof).
Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonwealth of Australia Mar. 3, 2016, (21 pages).
Declaration of Michael Armin Borowitzka In the matter of Australian Patent Application No. 2009303354 in the name of Solazyme, Inc. and Opposition by *Roquette Frères, S.A.* v. *Solazyme, Inc.*, Commonwealth of Australia Jun. 2, 2016, (32 pages).
• Exhibit MB-1, Federal Court of Australia, Practice Note CM7, Expert Witnesses in Proceedings on the Federal Court of Australia, commenes Jun. 4, 2013 • Exhibit MB-2, Michael Armin Borowitzka Curriculum Vitae • Exhibit MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. • Exhibit MB-4, Krauss, Robert W., "Mass Culture of Algae for Food and Other Organic Compounds," American Journal of Botany, vol. 49, No. 4 (Apr. 1962), pp. 425-435. • Exhibit MB-5, Lee, Yuan-Kun, "Commercial Production of microalgae in the Asia-Pacific rim", Journal of Applied Phycology, 9:403-411, (Oct. 29, 1997) • Exhibit MB-6, Soong, Pinnan, "Productions and Development of *Chlorella* and *Spirulina* in Taiwan", *Algae Biomass: Production and Use*, Gedaliah Shelef and Carl. J. Soeder (eds.), North-Holland Biomedical Press, (Dec. 1980), pp. 97-113 and title and copyright page. • Exhibit MB-7, Kawaguchi, Kotaro, "Microalgae Production Systems in Asia", *Algae Biomass: Production and Use*, Gedaliah Shelef and Carl J. Soeder eds.), North-Holland Biomedical Press, (Dec. 1980), pp. 25-33 and title and copyright page. • Exhibit MB-8, Kay, Robert A., "Microalgae as Food and Supplement", Critical Reviews in Food Science and Nutrition, 30(6):555-573 (Feb. 1991). • Exhibit MB-9, Raymundo et al., "Fat mimetic capacity of *Chlorella vulgaris* biomass in oil-in-water food emulsions stabilized by pea protein," Food Research International, 38:961-965, (Feb. 25, 2005). • Exhibit MB-10, Samejima, H. and J Myers, "On the Heterotrophic Growth of *Chlorella pyrenoidosa*", J. Gen Microbiol, (1958), 18:107-117.
• Exhibit MB-11, Aoki, Shigeji and Eiji Hase, "De- and Re-Generation of Chloroplasts in the Cells of *Chlorella protothecoides*", Plant & Cell Phyiol, (Sep. 5, 1964), vol. 5, pp. 473-484 [Retrieved from the internet on Jun. 7, 2013 from http://pcp.oxfordjournals.org/ by Reprints Desk ]. • Exhibit MB-12, Becker, E.W., "Micro-algae as a source of protein," Biotechnology Advances, 25:207-201, (Mar.-Apr. 2007). • Exhibit MB-13, Iwamoto, Hiroaki, "Industrial Production of Microalgal Cell-mass and Secondary Products—Major Industrial Species *Chlorella*", Chapter 11, Handbook of Microalgal Culture: Biotechnology and Applied Phycology, Amos Richmond (eds), (Dec. 1, 2003), pp. 255-263. • Exhibit MB-14, Petkov et al., "Which are fatty acids of the green alga *Chlorella*?," Biochemical Systematics and Ecology, 35:281-285, (2007). • Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21, 1995), 31:774-777. • Exhibit MB-16, Xu et al., "High Quality Biodiesel Production From a Microalga *Chlorella protothecoides* by Heterotrophic Growth In Fermenters," Journal of Biotechnology, 126(4):499-507, (May 2006). • Exhibit MB-17, Matsuka et al., "Changes in Contents of Carbohydrate and Fatty Acid in the Cells of *Chlorella protothecoides* during the process of De- and Re-Generation of Chloroplasts," Plant and Cell Physiol., 7:651-662 (Sep. 24, 1966). • Exhibit MB-18, Xuan, J. et al., "Removal of total nitrogen from wastewater discharge from a chemical fertilizer plant by *Chlorela protothecoides* USTB-01", Chinese Journal of Environmental Engineering, (Apr. 2010), vol. 4, No. 4, pp. 737-740.
• Exhibit MB-19, Australian Application No. 2009303354B2 from International Patent Application No. PCT/US2009/060692, naming Solazyme, Inc., International Patent Publication No. 2010/045368, dated Apr. 22, 2010. • Exhibit MB-20, Pabst, W., "Nutritional evaluation of nonsewage microalgae by the rat balance method," Arch. HyrobioL Beih, (Dec. 1978), pp. 65-70 • Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000).
• Exhibit MB-22, Kamiya, "Effects of Blue Light and Ammonia on Nitrogen Metabolism in a Colorless Mutant of Chlorella", Plant Cell Phyiol., 30(4):513-521 (1989) • Exhibit MB-23, Biello et al., "Biofuel of the Future: Oil from Algae," Scientific American, 2 pages, (Jan. 9, 2008).
Evidence in Support, In the matter of Australian Patent Application No. 2009303354 in the name of Solazyme, Inc. and Opposition by *Roquette Frères, S.A.* v. *Solazyme, Inc.*, Commonwealth of Australia, Jun. 3, 2016, (1 page).
Declaration of Young J. Suh In the matter of Australian Patent Application No. 2009303354 in the name of Solazyme, Inc. and Opposition by *Roquette Frères, S.A.* v. *Solazyme, Inc.*, Commonwealth of Australia, Aug. 31, 2016, (94 pages) • Exhibit YS1, Arbitration Award, *Solazyme Inc.* vs. *Roquette Frères*, Case 1:14-cv-O1442-SLR, Document 153, Filed Dec. 21, 2015 • Exhibit YS2, French Patent Publication No. FR 2 924 126, fded Nov. 28, 2007.
• Exhibit YS3, Memorandum Opinion, Document 153, *Roquette Frères, S.A.* vs. *Solazyme Inc.*, Case 1:14-cv-O1442-SLR, filed Dec. 21, 2015.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 5, 2016, (22 pages) • Exhibit CP-1, Federal Court of Australia, Practice Note CM7, Expert Witnesses in Proceedings on the Federal Court of Australia, commences Jun. 4, 2013. • Exhibit CP-2, Craig Patch Curriculum Vitae.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 28, 2016, (42 pages). • Exhibit CP3, Record of Views Formed in Response To Inquires, updated Mar. 2015 (20 pages) • Exhibit CP4, Huss, V.A.R., et al., "Biochemical Taxonomy and Molecular Phylogeny of the Genus *Chlorella* Sensu Lato (Chlorophyta)1", J. Phycol. 35, 587-598 (Jan. 15, 1999).
Evidence in Answer, In the matter of Australian Patent Application No. 2009303354 in the name of Solazyme, Inc. and Opposition by *Roquette Frères, S.A.* v. *Solazyme, Inc.*, Commonwealth of Australia, Sep. 29, 2016, (1 page).
Declaration of Michael Armin Borowitzka In the matter of Australian Patent Application No. 2009303354 in the name of Solazyme, (56) References Cited

OTHER PUBLICATIONS

Inc. and Opposition by *Roquette Frères, S.A.* v. *Solazyme, Inc.*, Commonwealth of Australia, Dec. 21, 2016, (14 pages).
Evidence in Reply, In the matter of Australian Patent Application No. 2009303354 in the name of Solazyme, Inc. and Opposition by *Roquette Frères, S.A.* v. *Solazyme, Inc.*, Commonwealth of Australia Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingredient-at-the-2013-fi-europe-excellence-awards, (Nov. 25, 2013), pp. 1-5.
Freshwater Algae Culture Collection at the Institute of Hydrobiology (FACHB-collection), certification letter by the Chinse Academy of Science, "*Chlorella vulgaris*", (No Date).
Zhou, Lian-ning et al. "Effects of Environmental Factors on Nitrogen and Phosphorus Removal by *Chlorella vulgaris* in Wastewater", Current Biotechnology, (Jan. 25, 2015), vol. 5, No. 1, Title page, Publication Page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17, 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent's Outline of Submissions, in the Matter of Australian Patent Application No. 2009303354 in the name of Corbion Biotech, Inc., dated Jan. 24, 2018, 48 pages.
Response To Reg 5.23 Request, in the Matter of Australian Patent Application No. 2009303354 in the name of Corbion Biotech, Inc., filed Feb. 5, 2018, 18 pages. • Letter from David Sieveking, dated Jan. 24, 2018 • Statutory Declaration of Dr. Daniel Peter Sieveking, dated Jan. 24, 2018. • Exhibit DS-1, Kyle, David, "Production and Use of Lipids from Microalgae", Microalgal Lipids, Lipid Technology, (May-Jun. 1992), pp. 59-64. • Exhibit DK-2, Chen et al., "High cell density culture of microalgae in heterotrophic growth," Trends In Biotechnology, 14:421-426, (1996).
Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only, [SOLAO043JP-0807X01JP].
Request for Withdrawal of Opposition, by Roquette Freres, to Grant of Australian Patent Application No. 2009303354, in the Name of Corbion Biotech, Inc., dated Mar. 13, 2018.
Opposition Proceedings, dated Mar. 14, 2018, Acknowledgement of the the Request for Withdrawal of Opposition, by Roquette Freres, to Grant of Australian Patent Application No. 2009303354.
Third Party Observations from Roquette Freres, dated Aug. 31, 2017, for Chinese patent for invention No. 200980149978.1 (in Japanese with English Translation).
Third Party Observations from Roquette Freres, dated Aug. 31, 2017, for Chinese patent for invention No. 201080026237.7 (in Japanese with English Translation).
Baker, J.E., et al., "Assimilation of Ammonia by Nitrogen-Starved Cells of Chlorella Vulgaris." Plant Physiology, (Mar. 1961), vol. 36(2), pp. 208-212.
Reisner, B. G. S., Gering, R. K., and J. F. Thompson. The metabolism of nitrate and ammonia by Chlorella. Plant Physiol., (1960), 35, 48-52.
Xiong, W., et al., "13C-Tracer and Gas Chromatography-Mass Spectrometり Analyses Reveal Metabolic Flux Distribution in the Oleaginous Microalga Chlorella Protothecoides." Plant Physiology, vol. 154, pp. 1001-1011 , Oct. 2010.
U.S. Appl. No. 15/963,945, filed Apr. 26, 2018, Segueilha et al.
U.S. Appl. No. 15/953,312, filed Apr. 13, 2018, Gabriel Macquart.

\* cited by examiner

METHOD FOR THE PROTEIN ENRICHMENT OF MICROALGAL BIOMASS

CROSS REFERENCE TO RELATED APPLICATION

This application is a U.S. national stage application of International Patent Application No. PCT/FR2016/050269, filed Feb. 8, 2016, the subject matter of which is incorporated in its entirety by reference herein.

The present invention relates to a method for the protein enrichment of microalgal biomass, more particularly of the *Chlorella* genus, even more particularly of the species *Chlorella protothecoides*.

Macroalgae and microalgae have a specific richness which remains largely unexplored. Their utilization for dietary, chemical or bioenergy purposes is still highly marginal. However, they contain components of great value, in terms of both richness and abundance.

Indeed, microalgae are sources of vitamins, lipids, proteins, sugars, pigments and antioxidants.

Algae and microalgae are thus of interest to the industrial sector, where they are used for manufacturing food supplements, functional foods, cosmetics and medicaments, or for aquaculture.

Microalgae are first and foremost photosynthetic microorganisms which colonize all biotopes exposed to light.

On the industrial scale, the monoclonal culturing thereof is performed in photobioreactors (autotrophic conditions: in light with $CO_2$) or, for some, it is also performed in fermenters (heterotrophic conditions: in darkness in the presence of a source of carbon).

Some species of microalgae are indeed able to grow in the absence of light: *Chlorella, Nitzschia, Cyclotella, Tetraselmis, Crypthecodinium, Schizochytrium*.

Moreover, it is estimated that culturing under heterotrophic conditions is 10 times less expensive than under phototrophic conditions because, for those skilled in the art, these heterotrophic conditions allow:

the use of fermenters identical to those used for bacteria and yeast, enabling all the culturing parameters to be controlled, the production of biomasses in much greater amounts than those obtained by light-based culturing.

The profitable utilization of microalgae generally necessitates controlling the fermentation conditions, making it possible to accumulate their components of interest, such as:

pigments (chlorophyll a, b and c, β-carotene, astaxanthin, lutein, phycocyanin, xanthophylls, phycoerythrin, etc.), the demand for which is increasing both due to their noteworthy antioxidant properties and to their provision of natural colorings for food, lipids, in order to optimize their fatty acids content (up to 60%, or even 80% by weight of their dry solids), especially for:
  biofuel applications, but also
  applications in food for human consumption or animal feed, when the selected microalgae produce "essential" (i.e. supplied by the diet because they are not naturally produced by humans or animals) polyunsaturated fatty acids or PUFAs, or proteins, in order to optimize the nutritive qualities thereof or, for example, to promote the supply of amino acids of interest.

In the context of supplying amino acids of interest, it may in fact be advantageous to have available protein sources that are rich in arginine and glutamate.

Arginine is an amino acid that has many functions in the animal kingdom.

Arginine may be degraded and may thus serve as a source of energy, carbon and nitrogen for the cell which assimilates it.

In various animals, including mammals, arginine is decomposed into ornithine and urea. The latter is a nitrogenous molecule that can be eliminated (via excretion in the urine) so as to regulate the amount of nitrogenous compounds present in the cells of animal organisms.

Arginine allows the synthesis of nitrogen monoxide (NO) via NO synthetase, thus participating in the vasodilation of the arteries, which reduces the rigidity of the blood vessels, increases the blood flow and thus improves the functioning of the blood vessels.

Food supplements which contain arginine are recommended for promoting the health of the heart, the vascular function, for preventing "platelet aggregation" (risk of formation of blood clots) and for lowering the arterial pressure.

The involvement of arginine in the healing of wounds is associated with its role in the formation of proline, which is another important amino acid in collagen synthesis.

Finally, arginine is a component that is frequently used, in particular by sportspeople, in energy drinks.

As regards glutamic acid, it is not only one of the elementary bricks used for protein synthesis, but is also the excitatory neurotransmitter that is the most widespread in the central nervous system (encephalon+spinal cord) and is a GABA precursor in GABAergic neurons.

Under the code E620, glutamate is used as a flavor enhancer in foods. It is added to food preparations to enhance their taste.

Besides glutamate, the Codex *Alimentarius* has also recognized as flavor enhancers the sodium salt (E621), the potassium salt (E622), the calcium salt (E623), the ammonium salt (E624) and the magnesium salt (E625) thereof.

Glutamate (or the salts thereof) is often present in ready-made meals (soups, sauces, crisps and ready-made dishes). It is also commonly used in Asian cookery.

It is currently frequently used in combination with flavorings in aperitifs (bacon flavor, cheese flavor). This makes it possible to enhance the bacon, cheese, etc. flavor. It is rare to find an aperitif not containing any.

It is also found in certain medicament capsules, but not for its taste functions.

Finally, it is the major component of cooking auxiliaries (stock cubes, sauce bases, sauces, etc.).

In order to achieve the exploitation of the metabolic richness of microalgae, first fermentation methods for obtaining high cell densities (HCD) were thus thoroughly investigated so as to obtain maximum protein or lipid yields and productivity.

The aim of these HCD cultures was to obtain the highest possible concentration of the desired product in the shortest possible period of time.

This principle is borne out for example by the biosynthesis of astaxanthin by *Chlorella zofingiensis*, in which growth of the microalga proved to be directly correlated with the production of this compound (Wang and Peng, 2008, World J. Microbiol. Biotechnol., 24(9), 1915-1922).

However, maintaining growth at its maximum rate (μ, in $h^{-1}$) is not always correlated with high production of the desired product.

Indeed, it quickly became apparent to specialists in the field that it is necessary, for example, to subject the microalgae to a nutritional stress which limits their growth, when it is desired to make them produce large lipid reserves.

Growth/production decoupling in fermentation methods and control of the rate of cell growth are thus now performed.

In general, those skilled in the art choose to control the growth of microalgae by controlling the fermentation conditions (temperature, pH, etc.) or by the regulated supply of nutritional components to the fermentation medium (semi-continuous conditions referred to as "fed batch").

If they choose to control the growth of microalgae heterotrophically through the supply of carbon sources, those skilled in the art generally choose to adapt the carbon source (pure glucose, acetate, ethanol, etc.) to the microalga (*C. cohnii*, *Euglena gracilis*, etc.) as a function of the metabolite produced (for example a polyunsaturated fatty acid of DHA type).

The temperature may also be a key parameter:
for example, it has been reported that the synthesis of polyunsaturated fatty acids in some species of microalgae, such as EPA by *Chlorella minutissima*, is promoted at a temperature lower than the one required for the optimal growth of said microalga;
on the other hand, the lutein yield is higher in heterotrophically cultivated *Chlorella protothecoides* when the production temperature is increased from 24 to 35° C.

Indeed, *Chlorella protothecoides* is acknowledged to be one of the best oil-producing microalgae.

Under heterotrophic conditions, it rapidly converts carbohydrates to triglycerides (more than 50% of dry matter).

To optimize this production of triglycerides, those skilled in the art are led to optimize the carbon flow toward oil production, by acting on the nutritional environment of the fermentation medium.

Thus, it is known that oil accumulates when there is a sufficient supply of carbon but under conditions of nitrogen deficiency.

Therefore, the C/N ratio is the determining factor here, and it is accepted that the best results are obtained by acting directly on the nitrogen content, with the glucose content not being a limiting factor.

Unsurprisingly, this nitrogen deficiency affects cell growth, which results in a growth rate 30% lower than the normal growth rate for the microalga (Xiong et al., *Plant Physiology*, 2010, 154, pages 1001-1011).

To explain this result, in the abovementioned article Xiong et al. demonstrate that if the *Chlorella* biomass is divided into its 5 main components, i.e. carbohydrates, lipids, proteins, DNA and RNA (representing 85% of the dry matter), while the C/N ratio has no impact on the content of DNA, RNA or carbohydrates, it becomes preeminent for the content of proteins and lipids.

Thus, *Chlorella* cells cultivated with a low C/N ratio contain 25.8% proteins and 25.23% lipids, whereas a high C/N ratio enables the synthesis of 53.8% lipids and 10.5% proteins possible.

To optimize its oil production, it is therefore essential for those skilled in the art to control the carbon flow by steering it toward oil production to the detriment of protein production; the carbon flow is redistributed and accumulates as lipid storage substances when the microalgae are placed in a nitrogen-deficient medium.

However, *Chlorella protothecoides* may also be advantageously chosen to produce protein.

Given the analysis done by those skilled in the art as regards management of the C/N ratio for oil production (a high C/N ratio is targeted), a person skilled in the art is therefore led to favor a low C/N ratio, and thus:

to supply a large amount of nitrogen source to the fermentation medium while keeping constant the carbon source feedstock, which will be converted into proteins, and
to stimulate the growth of the microalga.

It is thus chosen to modify the carbon flow toward protein (and hence biomass) production, to the detriment of storage lipid production.

The present invention relates to a method for the protein enrichment of microalgal biomass, more particularly of the *Chlorella* genus, even more particularly of the species *Chlorella protothecoides*.

The present invention relates to a method for the protein enrichment of the biomass of certain microalgae, more particularly of *Chlorella protothecoides*, the arginine and glutamine content of which proteins is remarkably high.

The present invention more particularly covers a method for producing a biomass of protein-enriched microalgae, characterized in that it consists in increasing the ammonium supply in a biomass which is previously deficient in nitrogen.

Specifically, in the context of the invention, the Applicant company has, on the other hand, chosen to explore a novel route by proposing an alternative solution to that conventionally envisioned by a person skilled in the art, or even the exact opposite of that which he would have chosen.

The invention thus relates to a method for the protein enrichment of a heterotrophically cultured microalga, the microalga being of the genus *Chlorella*, even more particularly *Chlorella protothecoides*, the heterotrophic culturing method comprising:
a first step directed toward limiting the ammonium supply so as to obtain a microalgal biomass with a protein content of less than 50% expressed as N.6.25, preferably less than 30%, preferentially between 20 and 25%;
a second step in which the ammonium supply in the fermentation medium is increased so as to obtain a protein content of greater than 50%, preferably greater than 60%, even more preferentially greater than 65%.

As will be illustrated below, a preferential embodiment of the method in accordance with the invention may consist in regulating the pH in the first step with an $NH_3/KOH$ mixture, thus limiting the ammonium supply and hence promoting the production of a small protein content, and then in using pH regulation with $NH_3$ alone in the second step, so as to resupply the fermentation medium with ammonium.

The $NH_3/KOH$ mixture will be such that it makes it possible to limit the ammonium supply. For example, for the same concentration of $NH_3$ between the first and second step, the mixture may comprise $NH_3/KOH$ ratios that are of the order of about 1:1, for instance about 70-45% $NH_3$ and 30-55% KOH, preferably about 65-55% v/v $NH_3$ and 35-45% KOH, the amounts being expressed in moles.

The term "about" is intended to mean a value range comprising plus or minus 10% of the indicated value, preferably plus or minus 5% thereof. For example, "about 10" means between 9 and 11, preferably between 9.5 and 10.5.

In this preferential embodiment, the $NH_3$ supply is then multiplied by about 1.5 to 2 and the speed of nitrogen consumption resulting therefrom is multiplied by 5.

This second step is a step during which the increase in the ammonium supply to a biomass which is previously deficient in nitrogen results in a sporadic overconsumption of this salt by this biomass and leads, remarkably, to the boost of the protein content, up to a content of greater than 50%, preferably greater than 60%, preferentially greater than 65% (percentages expressed as N.6.25).

It is thus found that the specific speed of nitrogen consumption, which falls to a value of less than 0.005 g/g/hour during the nitrogen deficiency phase increases to a value of more than 0.01 g/g/hour after the nitrogen deficiency has been lifted.

In a preferred embodiment, the growth rate is kept substantially constant. For example, during these two phases, the growth rate is kept at 0.07 h$^{-1}$ to 0.09 h$^{-1}$, preferably about 0.08 h$^{-1}$.

To illustrate this concept, the invention more specifically covers a method for heterotrophically culturing *Chlorella protothecoides*, comprising:

a batch phase after seeding the fermenter supplying 20 g/l of glucose, an exponential fed-batch phase with a growth rate set at 0.08 h$^{-1}$, started when the glucose supplied in the batch is totally consumed, during which the ammonium supply is limited by using pH regulation with the aid of a mixture of NH$_3$ and of KOH as mentioned above for the purpose of obtaining a biomass containing less than 25% protein (expressed as N.6.25), and then an exponential fed-batch phase with the same growth rate set at 0.08 h$^{-1}$, during which the ammonium deficiency is lifted by regulating the pH with the aid of a 100% ammonia solution.

For example, the second fed-batch phase in which the ammonium deficiency is lifted is initiated when about 2 kg of dry glucose have been introduced.

For the purposes of the invention, the essential criterion is clearly that the cellular stress brought about by the nitrogen deficiency of the fermentation medium, followed by the lifting of this stress, under quite specific conditions, trigger consumption of the nitrogen introduced to boost the protein content of the biomass produced.

This strategy therefore goes entirely against the technical preconception which considers that to increase the protein content of the biomass, it is absolutely imperative to increase the nitrogen supply from the start of culturing.

Moreover, these operating conditions are reflected here not only by an increase in the protein richness, but also lead to appreciably increasing the arginine and glutamate content thereof.

More particularly, as will be illustrated below, the heterotrophic culturing of microalgae of the species *Chlorella protothecoides* comprising a step of culturing with a nitrogen deficiency and then an ammonium pulse leads to producing more than 45% of glutamic acid and of arginine relative to the total amino acids.

Thus, the present invention also relates to a method for enriching the glutamic acid and/or arginine content of a heterotrophically cultured microalga, preferably a microalga of the species *Chlorella protothecoides*, the method comprising heterotrophic culturing of said microalga which comprises a step directed toward limiting the ammonium supply so as to obtain a protein-poor microalgal biomass, followed by a step in which the growth rate is maintained and the ammonium supply is increased.

These culturing conditions thus result in the preparation of a microalgal biomass comprising more than 45% of glutamic acid and arginine relative to the total amino acids.

The invention will be understood more clearly from the following examples which are intended to be illustrative and nonlimiting.

EXAMPLES

Example 1: Preparation of a Biomass of C. *Protothecoides* Rich in Protein with a High Content of Glutamic Acid and Arginine The strain used is a *Chlorella protothecoides* (strain CCAP211/8D—*The Culture Collection of Algae and Protozoa*, Scotland, UK).

Preculture:

150 mL of medium in a 500 mL Erlenmeyer flask;

Composition of the medium: 40 g/L of glucose+10 g/L of yeast extract.

Incubation is performed under the following conditions:

time: 72 h;

temperature: 28° C.;

shaking: 110 rpm (Infors Multitron Incubator).

Culturing in batch and then fed-batch mode

Preparation and Initial Batch Medium prepare and filter a mixture of KOH at 400 g/l (41%)/NH3 at 20% v/v (59%);

sterilize 20 L fermenter at 121° C./20 min;

inoculate with 2 conical flasks of 500 mL of preculture (OD$_{600\ nm}$ of 15);

regulation of the pH at 5.2 with the KOH/NH$_3$ mixture;

starting shaking speed of 300 rpm;

aeration: 15 L/min of air;

pO$_2$ regulation at 30% by modifying the shaking;

temperature: 28° C.

Feeding glucose: 500 g/L ammonium sulfate: 25 g/L monobasic sodium phosphate: 17 g/L monobasic potassium phosphate: 23 g/L magnesium sulfate heptahydrate: 20 g/L iron sulfate: 120 mg/L calcium nitrate: 610 mg/L solution of trace elements: 45 mL/L solution of vitamins: 3.6 mL/L

| solution of trace elements (for 2 liters) | |
|---|---|
| Ingredients | (g) |
| CuSO$_4$•5H$_2$O | 0.22 |
| ZnSO$_4$•7H$_2$O | 28 |
| MnSO$_4$•1H$_2$O | 16 |

-continued

| solution of trace elements (for 2 liters) | |
|---|---|
| Ingredients | (g) |
| $FeSO_4 \cdot 7H_2O$ | 2.2 |
| Citric acid | 60 |
| $H_2O$ qs | 2 |

| Solution of vitamins | |
|---|---|
| Ingredients | (g/l) |
| Thiamine HCl | 13.5 |
| Biotin | 0.7 |
| Pyridoxine | 6.75 |

Fermentation Procedure provide the equivalent of 20 g/L of glucose before inoculation when the glucose concentration=0 g/L, start feeding in glucose in fed-batch mode; use a flow rate that makes it possible to set the growth rate at 0.08 $h^{-1}$ regulate to pH 5.2 with the 41% KOH/59% $NH_3$ mixture when 2 kg of glucose have been consumed by the microalga, switch the system to pH regulation with $NH_3$ alone, when the biomass reaches 100 g/L by weight of dry matter, and about 3.5 kg of glucose have been fed in, the glucose feeding is stopped.

Results:

Two tests were performed under these same conditions and the results are given in table I and in the following graphs:

TABLE I

| | Test 1<br>F2 140519<br>Final titer (%)<br>(for 3.6 kg of<br>glucose consumed) | Test 2<br>F5 140623<br>Final titer (%)<br>(for 3.4 kg of<br>glucose consumed) |
|---|---|---|
| N.6.25 | 66.0 | 65.7 |
| Total amino acids | 44.7 | 43.2 |
| Content of Arg and Glu relative to the total amino acids | 46 | 47 |
| Total fatty acids | 10.2 | 10.1 |
| Total sugars | 20.3 | 21.7 |
| Color of the biomass | Yellow | Yellow |

Figure 1:
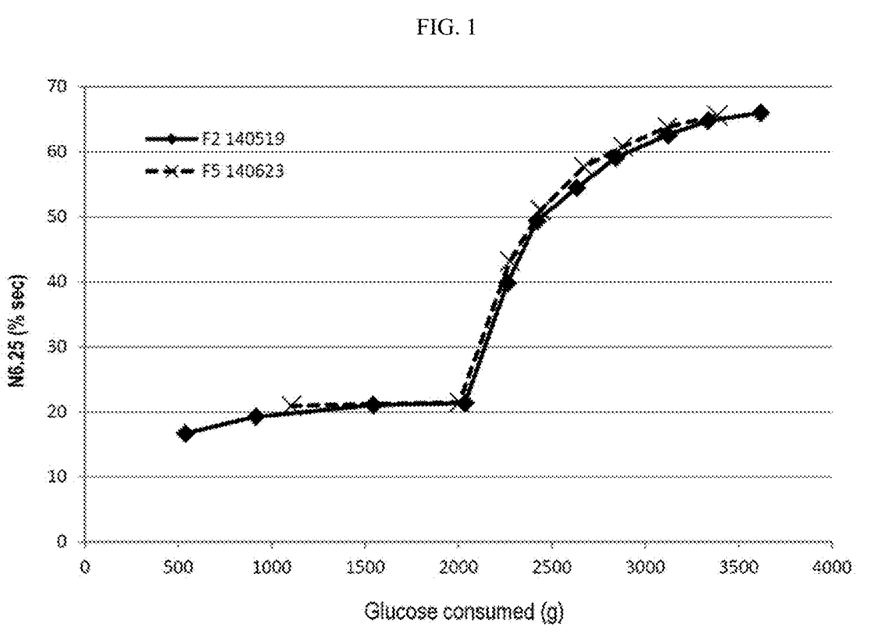
FIG. 1 illustrates the change in the N.6.25 as a function of the glucose consumed.

FIG. 1 illustrates the change in the N.6.25 as a function of the glucose consumed. These two tests reflect some noteworthy results: the production of a yellow biomass with an N.6.25 content of more than 65%.

Figure 2:
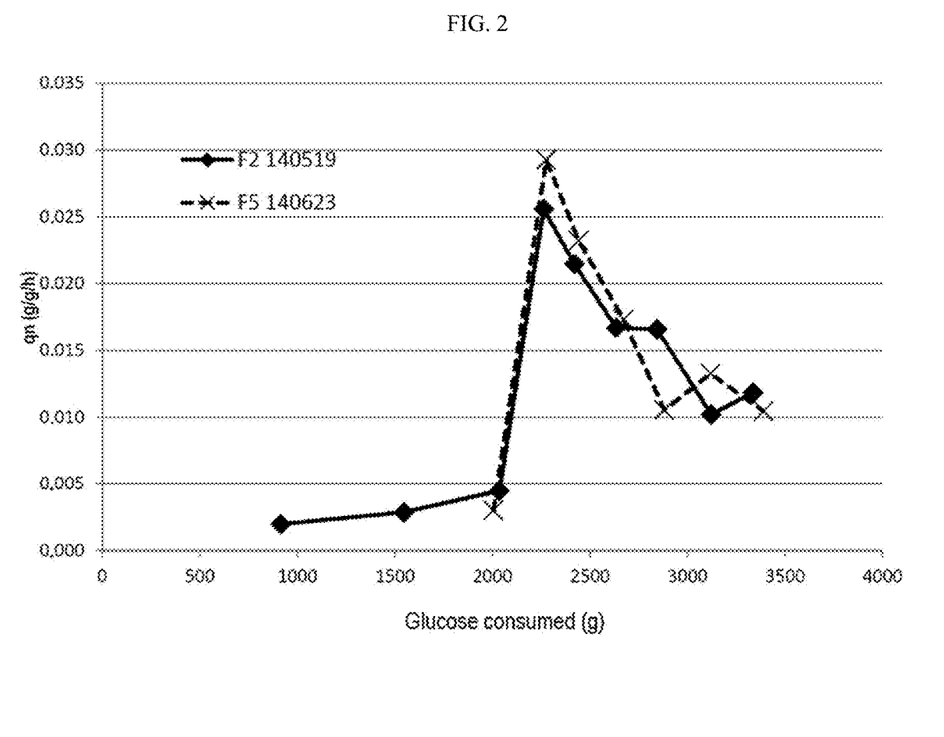
FIG. 2 illustrates the change in the specific rate of nitrogen consumption (qN) as a function of the glucose consumed.

FIG. 2 illustrates the change in the specific rate of nitrogen consumption (qN) as a function of the glucose consumed.

It is seen that the specific rate of nitrogen consumption is at its maximum after the nitrogen limitation has been lifted (at 2 kg of glucose consumed), and then decreases gradually. The similar rates between the two tests also reflect the good repeatability of the protocol.

Full analysis of the amino acids present in the biomass was performed on a sample taken just before lifting the limitation, and on several samples after the pulse.

Figure 3:
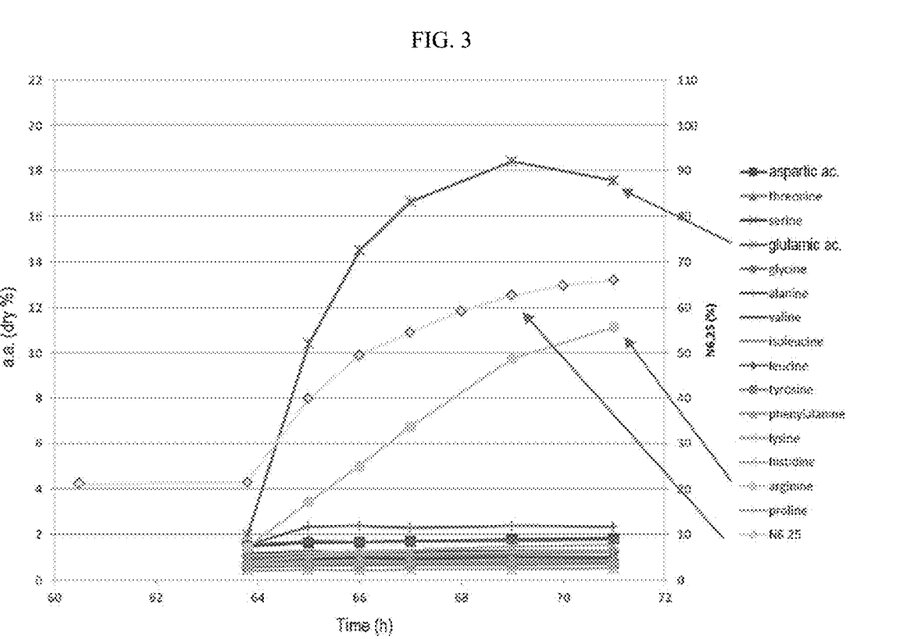
FIG. 3 illustrates the change in the N.6.25 as a function of time and the amount of each amino acid as a weight percentage of dry biomass as a function of time.

The results are shown in FIG. 3.

It is noted that just before lifting the nitrogen limitation, the sum of the amino acids is low (16.3%) and there is no predominance among the various amino acids.

One hour after lifting the nitrogen limitation, it is noted that the amino acid which undergoes the greatest increase is glutamic acid, followed by arginine. The content of the other amino acids also increases, but to a much lower extent.

The increase in the N.6.25 is thus above all correlated with the increase in glutamic acid and arginine.

In addition to these analyses, full analysis of the fatty acids present in the biomass was performed on a sample taken just before lifting the nitrogen limitation and on several samples after the pulse.

Figure 4:
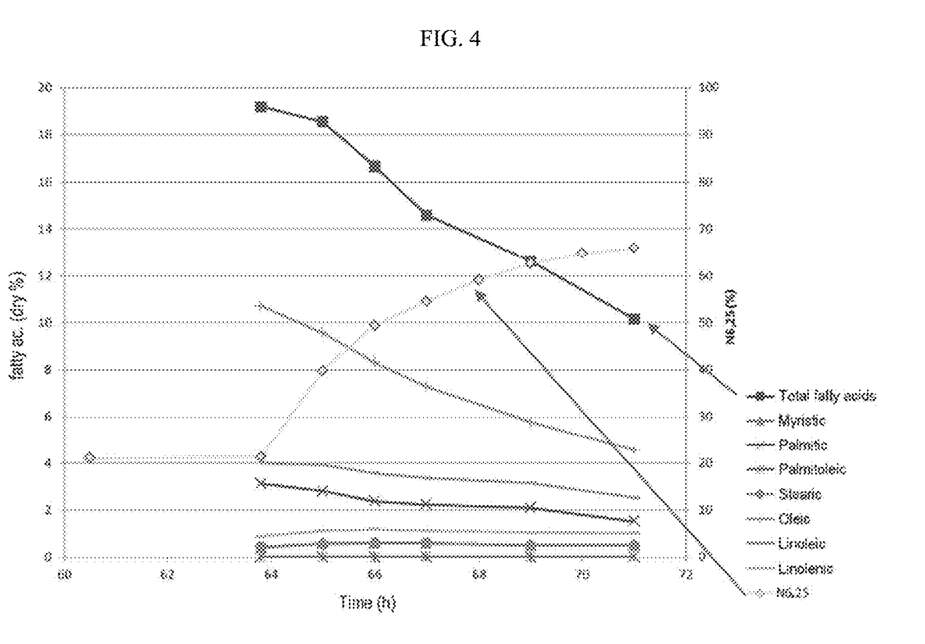
FIG. 4 illustrates the change in the N.6.25 as a function of time and the amount of total or particular fatty acids as a weight percentage of dry biomass as a function of time.

The results are shown in FIG. 4.

The total content of fatty acids in the biomass, which is 19.2% before the pulse, falls to 10.2%. The predominant fatty acid which follows this curve is oleic acid.

The fatty acids thus accumulate in the biomass when it is deficient in nitrogen.

Figure 5:
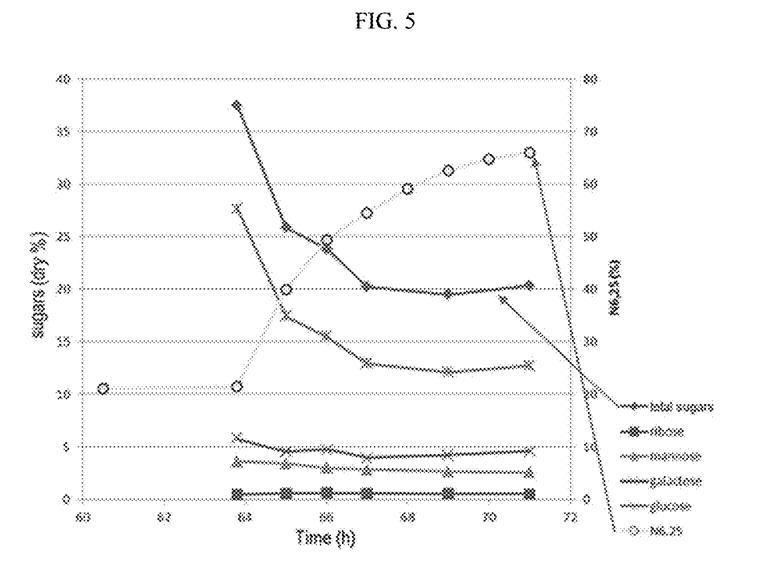
FIG. 5 illustrates the change in the N.6.25 as a function of time and the amount of total or particular sugars as a weight percentage of dry biomass as a function of time.

Full analysis of the sugars present in the biomass was also performed on a sample taken just before lifting the nitrogen limitation and on several samples after lifting the nitrogen limitation. The results are shown in FIG. 5.

The total content of sugars in the biomass, which is 37.5% before lifting the nitrogen limitation, falls to 20% and then stagnates. The predominant sugar which follows this curve is glucose.

The sugars are thus also stored in the biomass when it is deficient in nitrogen.

The content of sugars then appears to stabilize, unlike the fatty acid content which continues to decrease.

The salt content of the biomass was measured by measuring the calcination residue: it is 9%.

The invention claimed is:

1. A method for protein enrichment of heterotrophically cultured microalga of the genus *Chlorella*, the method comprising:
    a first step comprising cultivation of *Chlorella* in a fermentation medium, the fermentation medium comprising a limited supply of ammonia, wherein the microalga is cultivated to possess a protein content of less than 50% expressed as N.6.25, and wherein cultivation in the limited supply of ammonia provides a specific rate of nitrogen consumption by the microalga of less than 0.005 g/g/h; and
    a second step, wherein the ammonia present in the fermentation medium is increased, and wherein the microalga is cultivated until a protein content of a biomass of the microalga is increased to greater than 50% expressed as N.6.25.

2. The method as claimed in claim 1, wherein in the first step, pH regulation of the fermentation medium is performed by addition of an $NH_3$/KOH mixture, and wherein in the second step, pH regulation of the fermentation medium is performed with $NH_3$.

3. The method of claim 2, wherein a mole percent of the $NH_3$/KOH mixture is about 70-45% $NH_3$ and 30-55% KOH.

4. The method of claim 2, wherein a mole percent of the $NH_3$/KOH mixture is about 65-55% $NH_3$ and 35-45% KOH.

5. The method of claim 1, wherein the ammonia supply in the second step is increased by about 1.5 to 2 fold over the ammonia supply in the first step.

6. The method of claim 1, wherein in the second step, a specific rate of nitrogen consumption by the microalga is greater than 0.01 g/g/h.

7. The method of claim 1, wherein a growth rate of the microalga is maintained substantially constant during both the first step and the second step.

8. The method of claim 7, wherein the growth rate is maintained at 0.07 $h^{-1}$ to 0.09 $h^{-1}$.

9. The method of claim 8, wherein, the growth rate is maintained at about 0.0810.

10. The method of claim 1, wherein
the first step comprises a batch phase, wherein 20 g/l of glucose is supplied to a fermentation medium during cultivation of *Chlorella*, and;
a first exponential fed-batch phase, wherein a growth rate is maintained at 0.08 $h^{-1}$ until the glucose supplied in the batch phase is completely consumed;
wherein during the first exponential fed-batch phase, a concentration of ammonia in the fermentation medium is limited by regulating a pH of the fermentation medium with a mixture of NH3 and KOH, wherein during the first exponential fed-batch phase, biomass comprising less than 25% protein expressed as N.6.25 is obtained, and wherein the limited concentration of ammonia provides a specific rate of nitrogen consumption by the microalga of less than 0.005 g/g/h; and
the second step comprises a second exponential fed-batch phase, wherein the growth rate is maintained at 0.08 $h^{-1}$, and wherein during the second exponential fed-batch phase, the concentration of ammonia in the fermentation medium is no longer limited and the pH of the fermentation medium is regulated by adding 100% aqueous ammonia solution to the fermentation medium, and wherein during the second exponential fed-batch phase, biomass comprising more than 50% protein expressed as N.6.25 is obtained.

11. The method of claim 1, wherein
the microalgal biomass comprises 45% arginine relative to total amino acids of the biomass.

12. The method of claim 10, wherein
the microalgal biomass comprises 45% arginine relative to total amino acids of the biomass.

13. The method of claim 1, wherein the microalga is *Chlorella protothecoides*.

14. The method of claim 1, wherein the microalgal biomass comprises more than 45% of glutamic acid and arginine relative to the total amino acids of the microalgal biomass.

15. The method of claim 10, wherein the microalgal biomass comprises more than 45% of glutamic acid and arginine relative to the total amino acids of the microalgal biomass.

16. The method of claim 1, wherein the first step comprises cultivating the microalga until a protein content from 20 to 25% expressed as N.6.25 is obtained and the second step comprises cultivating the microalga until a protein content of the microalgal biomass is increased to greater than 60% expressed as N.6.25.

17. The method of claim 1, wherein the first step comprises cultivating the microalga until a protein content from 20 to 25% expressed as N.6.25 is obtained.

18. The method of claim 1, wherein the second step comprises cultivating the microalga until a protein content of the microalgal biomass is increased to greater than 60% expressed as N.6.25.

19. The method of claim 10, wherein during the second exponential fed-batch phase, biomass comprising more than 60% protein expressed as N.6.25 is obtained.

* * * * *

UNITED STATES PATENT AND TRADEMARK OFFICE
CERTIFICATE OF CORRECTION

PATENT NO. : 11,473,050 B2  
APPLICATION NO. : 16/074251  
DATED : October 18, 2022  
INVENTOR(S) : Le Ruyet et al.

Page 1 of 1

It is certified that error appears in the above-identified patent and that said Letters Patent is hereby corrected as shown below:

In the Claims

In Column 9, Claim 9, replace "0.0810" with "0.08 $h^{-1}$".

Signed and Sealed this  
Twenty-ninth Day of November, 2022

Katherine Kelly Vidal  
*Director of the United States Patent and Trademark Office*